(12) United States Patent
Pedalino et al.

(10) Patent No.: US 10,345,215 B1
(45) Date of Patent: Jul. 9, 2019

(54) FILTER TEST SYSTEM

(71) Applicants: Dean A. Pedalino, Clearwater, FL (US); Peter L. Day, Coral Springs, FL (US); John R. Bentley, II, Lakeland, FL (US)

(72) Inventors: Dean A. Pedalino, Clearwater, FL (US); Peter L. Day, Coral Springs, FL (US); John R. Bentley, II, Lakeland, FL (US)

(73) Assignee: Performance Assurance Systems LLC, Clearwater, FL (US)

( * ) Notice: Subject to any disclaimer, the term of this patent is extended or adjusted under 35 U.S.C. 154(b) by 167 days.

(21) Appl. No.: 15/241,825

(22) Filed: Aug. 19, 2016

(51) Int. Cl.
*G01N 15/08* (2006.01)

(52) U.S. Cl.
CPC ..... *G01N 15/0826* (2013.01); *G01N 15/0806* (2013.01); *G01N 2015/084* (2013.01)

(58) Field of Classification Search
CPC ........... G01N 15/0826; G01N 15/0806; G01N 2015/084
USPC .......................................................... 73/38
See application file for complete search history.

(56) References Cited

U.S. PATENT DOCUMENTS

| | | | | |
|---|---|---|---|---|
| 6,267,793 B1* | 7/2001 | Gomez | ................. | B01D 46/42 454/187 |
| 7,186,286 B2* | 3/2007 | Morse | ............... | B01D 46/0086 55/417 |
| 7,896,938 B2* | 3/2011 | Morse | ................ | B01D 46/0091 454/187 |
| 8,518,166 B2* | 8/2013 | Tasi | .................... | B01D 46/0086 55/385.2 |
| 9,976,770 B2* | 5/2018 | Cherry, Sr. | ............. | F24F 13/28 |
| 2004/0047776 A1* | 3/2004 | Thomsen | .................. | A61L 2/10 422/186.07 |
| 2006/0042359 A1* | 3/2006 | Morse | ................. | G01M 3/3281 73/40 |
| 2006/0272301 A1* | 12/2006 | Morse | ................ | B01D 46/0086 55/439 |
| 2008/0210000 A1* | 9/2008 | Yoshitome | .............. | F24F 3/161 73/198 |
| 2008/0216457 A1* | 9/2008 | Morse | .................. | B01D 46/008 55/502 |
| 2012/0272752 A1* | 11/2012 | Devine | ................... | A61L 2/186 73/863.01 |

* cited by examiner

*Primary Examiner* — Marrit Eyassu
(74) *Attorney, Agent, or Firm* — Paul Murty; Smith & Hopen, P.A.

(57) ABSTRACT

A filter has a rectilinear configuration with top and bottom surfaces, front and rear surfaces, and side surfaces. A ceiling has a coupling plate with a test port and a sensor port. Test equipment located below the ceiling is adapted to generate a flow of input aerosol. A coupling line is positioned between the test equipment and the test port. Sensor equipment is positioned below the ceiling and is adapted to sense a flow of output aerosol. An output line is positioned between the sensor equipment and the sensor port. First and second intermediate lines are operatively coupled between the test port and the filter and between the filter and the sensor port. An air conditioner line is operatively coupled to the top surface of the filter.

8 Claims, 5 Drawing Sheets

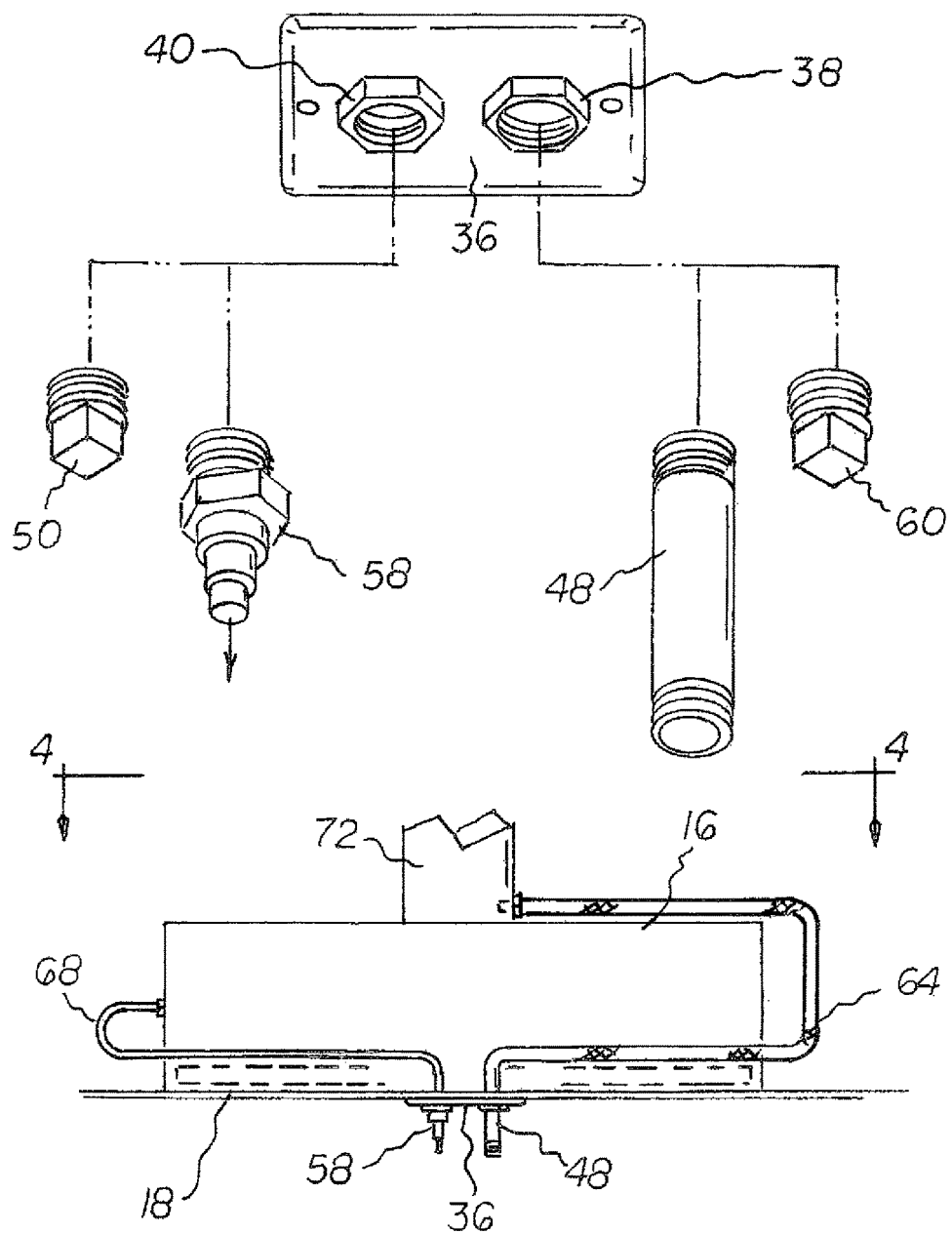

FIG. 6
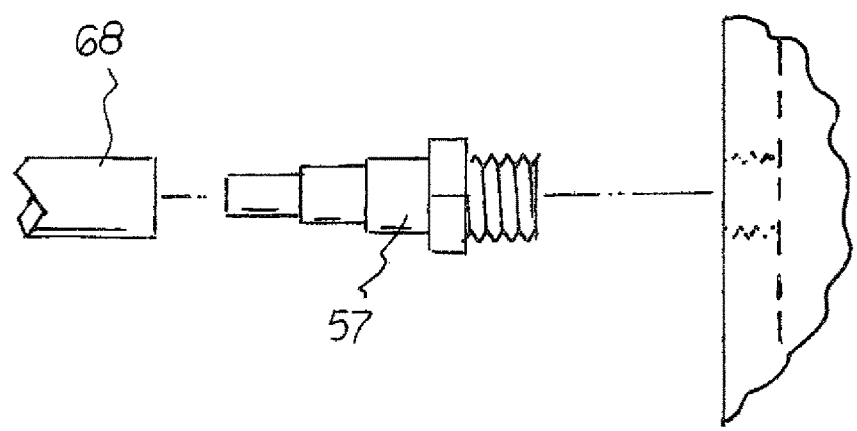
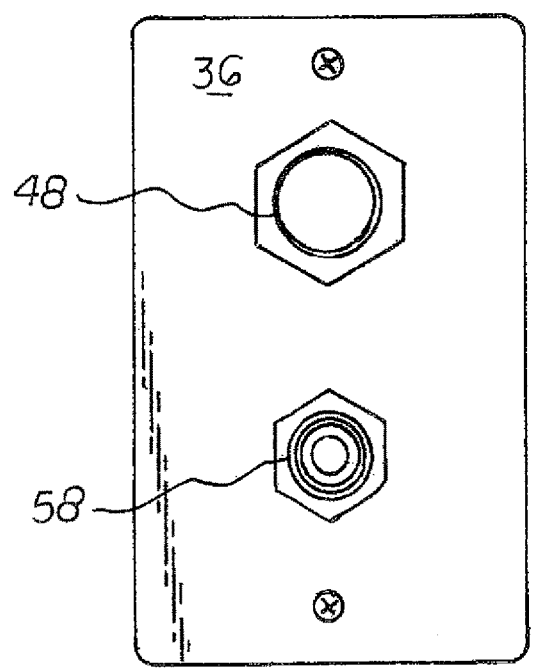
FIG. 7

FILTER TEST SYSTEM

BACKGROUND OF THE INVENTION

Field of the Invention

The present invention relates to a filter test system and more particularly pertains to coupling a filter to test equipment and to testing the filter, the coupling and the testing being done in a safe, convenient, and economical manner.

Description of the Prior Art

The use of filter test systems of known designs and configurations is known in the prior art. More specifically, filter test systems of known designs and configurations previously devised and utilized for the purpose of testing a filter are known to consist basically of familiar, expected, and obvious structural configurations, notwithstanding the myriad of designs encompassed by the crowded prior art which has been developed for the fulfillment of countless objectives and requirements.

While known devices fulfill their respective, particular objectives and requirements, they do not describe a filter test system that allows coupling test equipment to a filter and testing the filter with the test equipment, the coupling and the testing being done in a safe, convenient, and economical manner.

In this respect, the filter test system according to the present invention substantially departs from the conventional concepts and designs of the prior art, and in doing so provides an apparatus primarily developed for the purpose of coupling the filter to test equipment and for testing a high-efficiency particulate arrestance filter, the coupling and the testing being done in a safe, convenient, and economical manner.

Therefore, it can be appreciated that there exists a continuing need for a new and improved filter test system which can be used for coupling a filter to test equipment and for testing the filter, the coupling and testing being done in a safe, convenient, and economical manner. In this regard, the present invention substantially fulfills this need.

SUMMARY OF THE INVENTION

In view of the disadvantages inherent in the known types of filter test systems of known designs and configurations now present in the prior art, the present invention provides an improved filter test system. As such, the general purpose of the present invention, which will be described subsequently in greater detail, is to provide a new and improved filter test system and method which has all the advantages of the prior art and none of the disadvantages.

To attain this, from a broad perspective, the present invention essentially comprises a filter having a rectilinear configuration with top and bottom surfaces, front and rear surfaces, and side surfaces. A ceiling has a coupling plate with a test port and a sensor port. Test equipment located below the ceiling is adapted to generate a flow of input aerosol. A coupling line is positioned between the test equipment and the test port. Sensor equipment is positioned below the ceiling and is adapted to sense a flow of output aerosol. An output line is positioned between the sensor equipment and the sensor port. First and second intermediate lines are operatively coupled between the test port and the filter and between the filter and the sensor port. An air conditioner line is operatively coupled to the top surface of the filter.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved filter test system which has all of the advantages of the prior art filter test systems of known designs and configurations and none of the disadvantages.

It is another object of the present invention to provide a new and improved filter test system which may be easily and efficiently manufactured and marketed.

It is a further object of the present invention to provide a new and improved filter test system which is of durable and reliable constructions.

An even further object of the present invention is to provide a new and improved filter test system which is susceptible of a low cost of manufacture with regard to both materials and labor, and which accordingly is then susceptible of low prices of sale, thereby making such filter test system economically available.

Lastly, it is an object of the present invention to provide a filter test system for testing a high-efficiency particulate arrestance filter and for coupling the filter to test equipment, the coupling and testing being done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is an enlarged side elevational view of the coupling plate coupling hardware shown in FIG. 1.

FIG. 3 is a side elevational view of the filter and associated components shown in FIGS. 1 and 2.

FIG. 6 is an enlarged exploded view taken at circle 6 of FIG. 4.

FIG. 7 is a plan view of the coupling plate illustrated in the prior Figures.

The same reference numerals refer to the same parts throughout the various Figures.

DESCRIPTION OF THE PREFERRED EMBODIMENT

Figure 1:
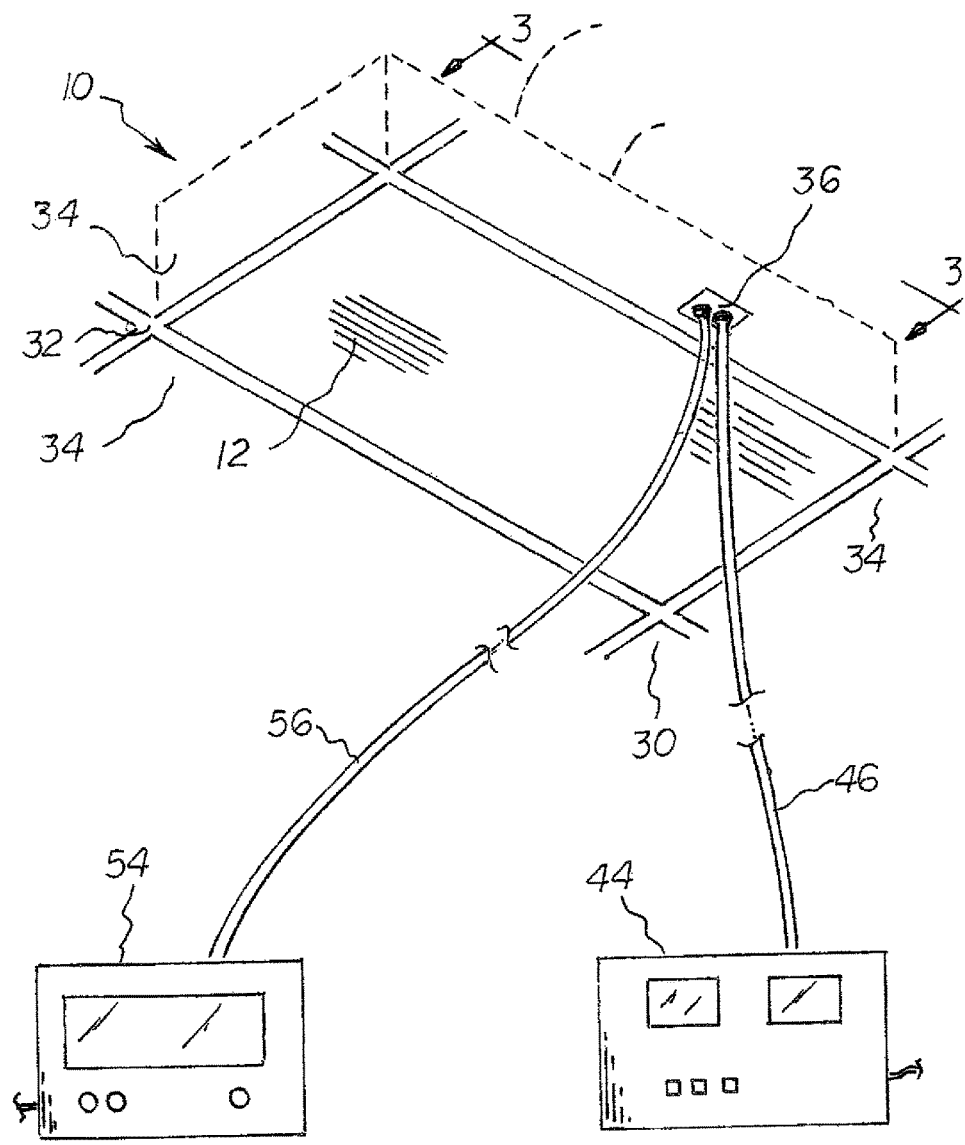
FIG. 1 is a perspective illustration of a high-efficiency particulate arrestance filter test system and associated equipment constructed in accordance with the principles of the present invention.
Figure 4:
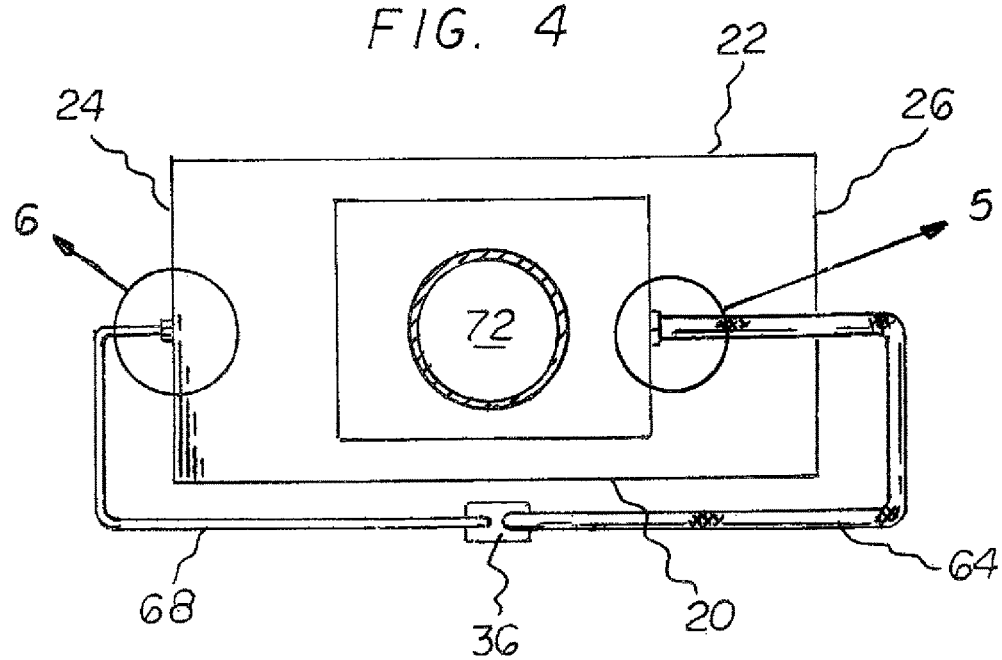
FIG. 4 is a plan view of the filter and associated components shown in the prior Figures.
Figure 5:
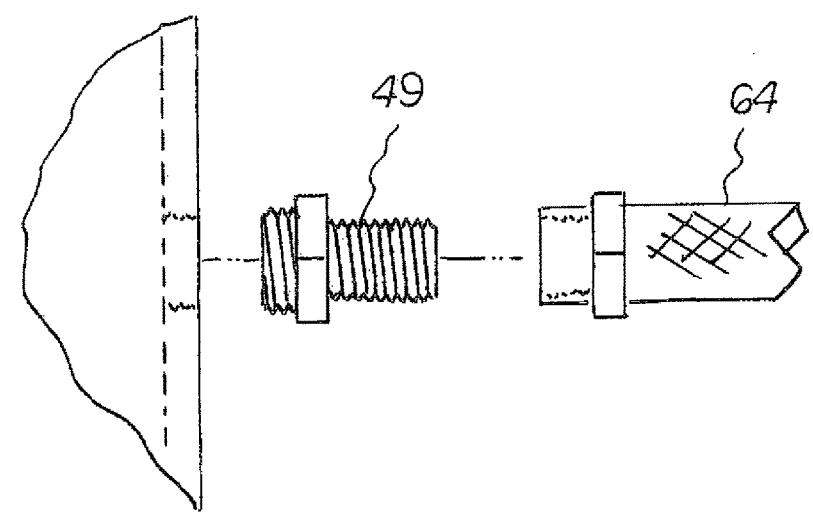
FIG. 5 is an enlarged exploded view taken at circle 5 of FIG. 4.

With reference now to the drawings, and in particular to FIG. 1 thereof, the preferred embodiment of the new and improved filter test system embodying the principles and concepts of the present invention and generally designated by the reference numeral 10 will be described.

The present invention, the filter test system 10, is comprised of a plurality of components. such components in their broadest context include a filter, a ceiling, a plate with test and sensor ports, test and sensor equipment, first and second lines, and an air conditioner line. Such components are individually configured and correlated with respect to each other so as to attain the desired objective.

From a specific perspective, the invention of the present application is filter test system 10 for coupling a filter to test equipment and for testing a high-efficiency particulate arrestance filter 12. The coupling and the testing are done in a safe, convenient, and economical manner. The system comprises, in combination, a high-efficiency particulate arrestance filter 12 having a rectilinear configuration with a top surface 16 and a parallel bottom surface 18. The high-efficiency particulate arrestance filter also has a front surface 20 and a parallel rear surface 22, and a left side surface 24 and a parallel right side surface 26. The high-efficiency particulate arrestance filter is adapted to be positionable to intercept a flow of air downwardly from the top surface toward the bottom surface and entrap particulate material passing through the high-efficiency particulate arrestance filter.

Next provided is a ceiling 30 constructed to include a frame 32 in a grid pattern with the high-efficiency particulate arrestance filter supported by the frame. A plurality of ceiling panels 34 are supported by the frame and surround the high-efficiency particulate arrestance filter. It should be understood that any of a plurality of ceiling constructions may be utilized such as a solid ceiling, for example.

In the disclosed primary embodiment, coupling plate 36 is positioned in one of the plurality of panels adjacent to the high-efficiency particulate arrestance filter. Repositioning the coupling plate to another location, such as a wall, is also possible. A test port 38 is in the coupling plate with an input end beneath the ceiling and an output end above the ceiling.

A sensor port 40 is in the coupling plate with an input end above the ceiling and an output end below the ceiling.

Test equipment 44 is positioned below the ceiling adapted to generate a flow of input aerosol. An input line 46 couples the test equipment and the test port. An input connector 48 is positioned between the input line and the input side of the test port during operation and use. An input stopper 50 is positioned in the input side of the test port when not during operation and use.

Sensor equipment 54 is provided below the ceiling adapted to sense a flow of output aerosol. An output line 56 couples the sensor equipment 52 and the sensor port. Sensor equipment is held beneath the sensor port to sense the aerosol. An output connector 58 is positioned between the output line and the output side of the sensor port during operation and use. An output stopper 60 is positioned in the output side of the sensor port when not during operation and use.

A first intermediate line 64 is operatively coupled between the test port and an air conditioner line 72 to the high-efficiency particulate arrestance filter through a primary filter fitting 49.

A second intermediate line 68 is operatively coupled between the sensor port and the left side surface of the high-efficiency particulate arrestance filter through a primary filter fitting 57.

Lastly, the air conditioner line 72 is operatively coupled to the top surface of the high-efficiency particulate arrestance filter to move air downwardly through the high-efficiency particulate arrestance filter. When aerosol is introduced to the high-efficiency particulate arrestance filter, through the input port toward the output port, if no aerosol is observed coming through the high-efficiency particulate arrestance filter then it is determinative that the integrity of the high-efficiency particulate arrestance filter is intact indicating that transmission of bacteria through the high-efficiency particulate arrestance filter is precluded, but if aerosol is observed leaking through the high-efficiency particulate arrestance filter then the high-efficiency particulate arrestance filter is compromised indicating that transmission of bacteria through the high-efficiency particulate arrestance filter is not precluded.

The present invention functions to allow ceiling mounted high-efficiency particulate arrestance filters mounted in a sterile clean environment to be leak tested, aerosol tested, without having to generate foreign particulates in the rooms due to having to lift or break ceiling mounted tiles which have been permanently affixed to the ceiling grid in accordance with USP 797 guidelines or having to penetrate solid ceiling surfaces. High-efficiency particulate arrestance filters are frequently referred to as HEPA filters. The system of the present invention allows access to filters from inside a room via access ports mounted to the ceiling in the primary embodiment.

In operation, a tester of a testing company may access an inside large fitting of the filter by removing the plug from the fitting and inserting the 0.75 inches threaded pipe into the fitting. This will allow connection to the test equipment which will introduce aerosol directly into the filter. The tester will then remove the plug from the outside of the filter and then insert the 0.375 inch stainless barbed fitting into the threaded receptacle. The purpose of the sensor port is to prove that aerosol is reaching the filter. All filter testing is completed at the filter. This will allow the user to attach their test equipment to the outside and take measurements across the pressure gradient of the filter.

Figure 8:
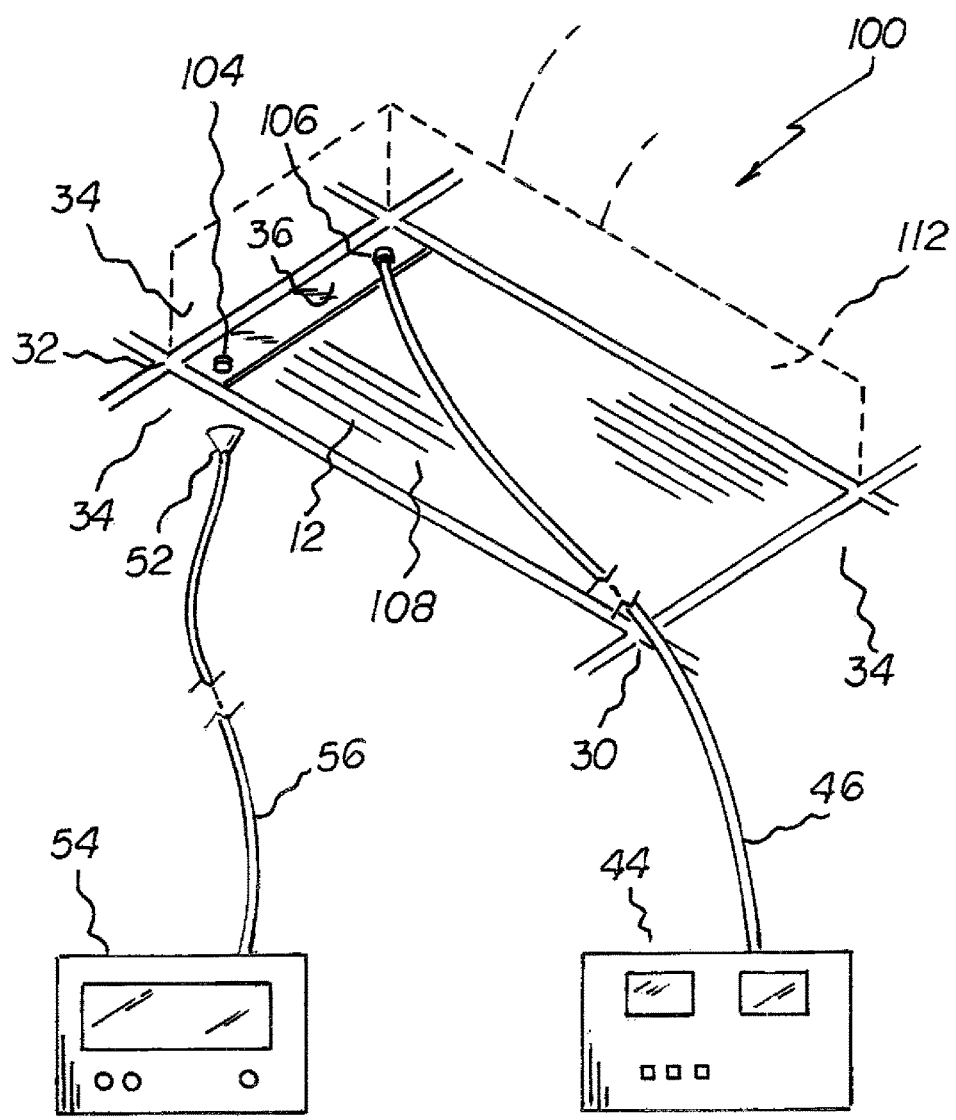
FIG. 8 is a perspective illustration of a high-efficiency particulate arrestance filter test system and associated equipment constructed in accordance with an alternate embodiment of the present invention.

An alternate embodiment of the high-efficiency particulate arrestance filter test system 100 and associated equipment is shown in FIG. 8. This alternate embodiment of the invention is similar to embodiments of the prior Figures except for the locations of the sensor port 104 and the test port 106. These ports are positioned on the bottom or output surface 108 of the high-efficiency particulate arrestance filter 112. The sensor port and the test port are manufactured into the filter housing in this embodiment.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A filter test system comprising:
    a filter having a rectilinear configuration with top and bottom surfaces, and front and rear surfaces, and right and left side surfaces, with a filter medium disposed between the top and bottom surfaces, the filter at least partially disposed in a space above a ceiling;
    a coupling plate with a test port and a sensor port, the coupling plate configured to provide access from a space beneath the ceiling to the space above the ceiling via the test port and the sensor port;
    test equipment disposed in the space below the ceiling configured to generate a flow of a test substance, a coupling line coupled to the test equipment and separably coupled to the test port;
    sensor equipment disposed in the space below the ceiling configured to sense a flow of the test substance, an output line coupled to the sensor equipment and separably coupled to the sensor port;
    an air conditioner line coupled to the top surface of the filter, the air conditioner line configured to translate air toward the filter medium and into the space beneath the ceiling, such that the filter medium is downstream from the air conditioner line with respect to air flow direction;
    a first intermediate line coupled between the test port and the air conditioner line, the first intermediate line being disposed upstream from the filter medium with respect to air flow, the first intermediate line configured to introduce the test substance to the air conditioner line to test the filter medium's performance;
    a second intermediate line coupled between the sensor port and the filter, the second intermediate line being disposed upstream from the filter medium with respect to air flow, the second intermediate line configured to detect an amount of the test substance adjacent to and upstream from the filter medium,
    wherein the amount of the test substance detected via the second intermediate line is comparable to an amount of the test substance detected downstream from the filter medium in the space beneath the ceiling to improve the accuracy of the filter test.

2. The system as set forth in claim 1 wherein the air conditioner line functions to move air from above the filter then downwardly through the filter towards a room there below, and wherein when the test substance is introduced to the filter, through the test port toward the sensor port, if no test substance is observed downstream from the filter medium then it is determinative that the integrity of the filter is intact indicating that transmission of bacteria through the filter is precluded, but if the test substance is observed downstream from the filter medium then the filter is compromised indicating that transmission of bacteria through the filter is not precluded.

3. The system as set forth in claim 2 wherein the coupling plate is positioned in the ceiling.

4. An improved high efficiency particulate air (HEPA) filter testing system used in combination with a room having a ceiling and a space above the ceiling, the HEPA filter being disposed at least partially above the ceiling, the testing system comprising:
    a coupling plate disposed within the ceiling and designed to provide access to the space above the ceiling, the coupling plate including a test port and a sensor port, each port providing a through-hole through which equipment couples to the HEPA filter;
    a first intermediate line coupled between the test port and an air conditioner line disposed in the space above the ceiling, the air conditioner line disposed upstream from the HEPA filter with respect to air flow, such that that air conditioner line is configured to translate air toward the HEPA filter and into the room beneath the ceiling;
    a second intermediate line coupled between the sensor port and the HEPA filter, the second intermediate line being downstream from a connection between the first intermediate line and the air conditioning line, and upstream from the HEPA filter; and
    an amount of a test substance configured to be introduced into the system via the first intermediate line, the test substance disposed to test the performance of the HEPA filter,
    wherein the second intermediate line is configured to the detect the amount of the test substance disposed adjacent to and upstream from the HEPA filter.

5. The testing system of claim 4, further comprising a test equipment disposed in the room beneath the ceiling, the test equipment coupled to the air conditioning line.

6. The testing system of claim 5, wherein the amount of the test substance is introduced to the air conditioning line from the test equipment via the first intermediate line.

7. The testing system of claim 4, further comprising a sensor equipment disposed in the room beneath the ceiling, the sensor equipment coupled to the HEPA filter.

8. The testing system of claim 7, wherein the amount of the test substance is detected by the sensor equipment via the second intermediate line.

* * * * *